United States Patent [19]

Kendell

[11] Patent Number: 4,950,230

[45] Date of Patent: Aug. 21, 1990

[54] METHOD AND APPARATUS FOR BAGLESS CONTINUOUS AMBULATORY PERITONEAL DIALYSIS

[75] Inventor: Lamar C. Kendell, Englishtown, N.J.

[73] Assignee: Delmed, Inc., Freehold, N.J.

[21] Appl. No.: 327,418

[22] Filed: Mar. 20, 1989

Related U.S. Application Data

[63] Continuation of Ser. No. 27,760, Mar. 19, 1987, abandoned.

[51] Int. Cl.⁵ .............................................. A61M 1/00
[52] U.S. Cl. ........................................ 604/28; 604/29; 604/32; 604/248; 137/625.41
[58] Field of Search ...................... 604/248, 27, 28, 29, 604/32, 49, 245; 137/625.47, 625.41

[56] References Cited

U.S. PATENT DOCUMENTS

| | | |
|---|---|---|
| 1,215,512 | 2/1917 | Fetzer .................................. 604/248 |
| 1,710,540 | 4/1929 | Hollander . |
| 1,853,202 | 4/1932 | Catlin . |
| 2,157,614 | 5/1939 | Lazarus . |
| 2,564,977 | 8/1951 | Hu . |
| 3,048,192 | 8/1962 | Murphy, Jr. . |
| 3,078,848 | 2/1963 | Milbert . |
| 3,678,959 | 7/1972 | Liposky . |
| 3,780,736 | 12/1973 | Chen . |
| 4,082,095 | 4/1978 | Mendelson ............................ 604/32 |
| 4,219,021 | 8/1980 | Fink ...................................... 604/93 |
| 4,239,041 | 12/1980 | Popovich . |
| 4,456,223 | 6/1984 | Ebling . |
| 4,471,942 | 9/1984 | Kocanowski . |
| 4,566,480 | 1/1986 | Parham . |
| 4,593,717 | 6/1986 | Levasseur ........................... 604/248 |
| 4,662,868 | 5/1987 | Cambio, Jr. ......................... 604/32 |

Primary Examiner—C. Fred Rosenbaum
Assistant Examiner—Kathleen A. Daley
Attorney, Agent, or Firm—Panitch, Schwarze, Jacobs & Nadel

[57] ABSTRACT

A method and apparatus for bagless continuous ambulatory peritoneal dialysis comprising a valve having first, second and third fluid ports. The first and second fluid ports are secured to first and second fluid containers, respectively, through tubing and respective first and second connector assemblies. The third fluid port is connected through tubing to a catheter implanted in the abdominal wall of a user, also through a connector assembly. The valve includes an actuator moveable at least between four positions, a first position in which all of the fluid ports are blocked to prevent the flow of fluid through the valve, a second position in which the second and third fluid ports are interconnected, a third position in which the first and second fluid ports are interconnected, and a fourth position in which the first and third fluid ports are interconnected. The method employs the valve to provide bagless continuous ambulatory peritoneal dialysis by reversing the fluid containers and the direction of movement of the valve actuator for alternate cycles.

6 Claims, 4 Drawing Sheets

METHOD AND APPARATUS FOR BAGLESS CONTINUOUS AMBULATORY PERITONEAL DIALYSIS

This application is a continuation of application Ser. No. 07/,027,760 now abandoned, filing date 3/19/87.

BACKGROUND OF THE INVENTION

The present invention relates to continuous ambulatory peritoneal dialysis ("CAPD") and continuous cycling peritoneal dialysis (CCPD), more particularly, to a method and apparatus for "bagless" CAPDCCPD.

CAPD was first developed in the mid-1970's for the removal of toxins from the body of a patient while the patient is permitted to remain totally ambulatory. The process involves the infusion of a dialysate fluid under prescribed conditions into the peritoneal cavity of the patient. The dialysate fluid remains in the peritoneal cavity for an extended residence period, typically four to five hours. During the residence period, toxic solutes are transported across the peritoneum and into the dialysate fluid by the natural processes of diffusion and convection while the patient goes about his normal activities. After the prescribed residence period, the dialysate fluid, along with the toxins, are removed from the peritoneal cavity for disposal and a new or fresh supply of dialysate fluid is infused into the peritoneal cavity. Further general information concerning CAPD can be obtained by referring to U.S. Pat. No. 4,239,041 of Popovich et al., entitled, "Method for Continuous Ambulatory Peritoneal Dialysis," the disclosure of which is incorporated herein by reference.

In the past, various methods and apparatus have been employed for performing bagless CAPD. In one such method, shown in the aforementioned U.S. patent, a bottle or bag of dialysate fluid is initially suspended at a height greater than the height of the peritoneal cavity of the patient. A first length of flexible tubing extends between an opening in the lower portion of the dialysate fluid bag to one port of a "Y" connector. A second length of flexible tubing extends from a second port of the "Y" connector to a catheter which has been surgically implanted in the abdominal wall of the patient. A third length of tubing interconnects the third port of the "Y" connector and an empty collection bottle or bag. Flow control clamps are provided on each of the three sections of tubing.

In explaining CAPD methods, it is normal to begin with the portion of the CAPD cycle which involves the fluid residence or "dwell" period. Therefore, in operation of the prior art apparatus, once the dwell period has been completed, the first and third tubes are connected to the "Y" connector and the clamps are removed from the second and third tubes, permitting the dialysate fluid and the toxins to drain from the peritoneal cavity through the catheter, through the second tube, through the "Y" connector, through the third tube and into the collection bag which is positioned at a level below that of the catheter. Once the drainage has been completed, the clamps are reinstalled on the second and third tubes, the full collection bag is removed, emptied and reconnected to the distal end of the third tube. A new, full bag or bottle of fresh dialysate fluid is connected to the distal end of the first tube. The clamps on the first and second tubes are removed, thereby permitting fluid from the full dialysate bottle or bag to flow by gravity through the first tube, through the "Y" connector, through the second tube, through the catheter and into the peritoneal cavity. The clamps are then reapplied to both the first and second tubes and the first and third tubes are disconnected from the "Y" connector to provide freedom of movement to the user during the dwell period.

While the prior art method and apparatus for CAPD is generally adequate, there are disadvantages to the use of apparatus of this type in which the tubing is clamped to prevent fluid flow. It has been determined that in some cases the clamping of the tubing results in kinks or other damage to the tubing which could obstruct or otherwise impede the proper flow of the fluid either into or out of the peritoneal cavity. In addition, it has been found that on some occasions, patients inadvertently removed all three of the clamps at the same time, resulting in the improper flow of dialysate fluid and possible contamination. Moreover, with some patients, particularly patients with severe arthritis, it is difficult for the patient to actuate the clamps. The manual sequence of opening and closing multiple clamps is confusing to some users and could result in improper fluid flows.

The present invention provides an improved method and apparatus for bagless CAPD which employs a special three-way valve for directing the flow of dialysate fluid into and out of the peritoneal cavity. The apparatus of the present invention employes no clamps so that kinking or other damage to the interconnecting tubing is avoided. In addition, the three-way valve of the present invention is simple to operate and precludes inadvertent interconnection of the various tubes, thereby preventing undesired fluid flows and/or contamination.

The present invention is also adapted to be utilized with continuous cycling peritoneal dialysis (CCPD) by employing large-sized fluid containers.

SUMMARY OF THE INVENTION

Briefly stated, the present invention comprises an apparatus for peritoneal dialysis comprising a valve having first, second and third fluid ports. A first tube has one end secured to the first port and the other end secured to a first connector member. The first connector member is adapted to be connected to a mating connector member associated with a first fluid container to provide fluid communication between the first port and the first fluid container. A second tube has one end secured to the second port and the other end secured to a second connector member. The second connector member is adapted to be connected to a mating connector member associated with a second fluid container to provide fluid communication between the second port and the second fluid container. A third tube has one end secured to the third port and the other end secured to a third connector member. The third connector member is adapted to be connected to a mating connector member associated with a catheter implanted in the abdominal wall of a user to provide communication between the third port and the peritoneal cavity of the user. The valve includes an actuator which is moveable between at least four positions.

In the first position, all of the ports are blocked to prevent fluid flow through the valve. In a second position, the second and third ports are interconnected to provide fluid communication therebetween and between the peritoneal cavity of the user and the second fluid container. In a third position of the actuator, the first and second ports are interconnected to provide fluid communication therebetween and between the first and second fluid containers. In a fourth position of the valve actuator, the first and third ports are interconnected to provide fluid communication therebetween and between the first fluid container and the peritoneal cavity of the user.

In employing the method of the present invention, the first fluid container initially contains fresh dialysate fluid and is supported at a height above the peritoneal cavity of the user, and the second fluid container is generally empty and is supported at a position below the peritoneal cavity. Dialysate fluid is in the peritoneal cavity of the user for a dwell period. When the dialysate dwell period has been completed, the third connector member is connected to its mating connector member with the valve actuator in the first position and the valve actuator is moved to the second position to permit the used dialysate fluid to drain from the peritoneal cavity into the second fluid container. When the dialysate fluid has drained into the second fluid container, the valve actuator is moved to the third position to permit dialysate fluid to flow from the first fluid container to the second fluid container to flush the valve and tubes. The valve actuator is then moved to the fourth position to permit dialysate fluid to flow from the first fluid container into the peritoneal cavity. At the same time, the second connector member is disconnected from its mating connector for disposal of the second container. The second connector member is reconnected to a mating connector member associated with a new second fluid container having a fresh supply of dialysate fluid.

When all of the dialysate fluid has been infused into the peritoneal cavity, the valve actuator is moved to the first position, the second fluid container member is supported at a height above the peritoneal cavity of the user and the empty first fluid container is moved to a position below the level of the peritoneal cavity. The third connector member is disconnected from its mating connector member during a dialysis dwell period.

When the dwell period has been completed, the third connector member is reconnected to its mating connector member and the valve actuator is moved to the fourth position for draining the fluid from the peritoneal cavity into the first fluid container. When all of the fluid from the peritoneal cavity has drained, the valve actuator is moved to the third position to permit dialysate fluid to flow from the second fluid container through the valve to the first fluid container to flush the system. The valve actuator is then moved to the second position to permit the dialysate fluid to flow from the second container into the peritoneal cavity. At the same time the first connector member is disconnected from its mating connector member and the first fluid container for disposal. Thereafter, the first connector member is connected to a mating connector member associated with a new first fluid container containing fresh dialysate fluid. When the infusion of dialysate fluid has been completed, the valve actuator is moved to the first position and the third connector member is disconnected from its mating connector member for the dwell period. The first fluid container is also moved to a level above the peritoneal cavity and the second fluid container is moved to a level below the peritoneal cavity. The process is then repeated as described above.

BRIEF DESCRIPTION OF THE DRAWINGS

The foregoing summary, as well as the following detailed description of preferred embodiments of the invention, will be better understood when read in conjunction with the appended drawings. It will be appreciated that the present invention is not limited to the specific embodiment and instrumentalities shown in the drawings. In the drawings.

DESCRIPTION OF PREFERRED EMBODIMENTS

Figure 1:
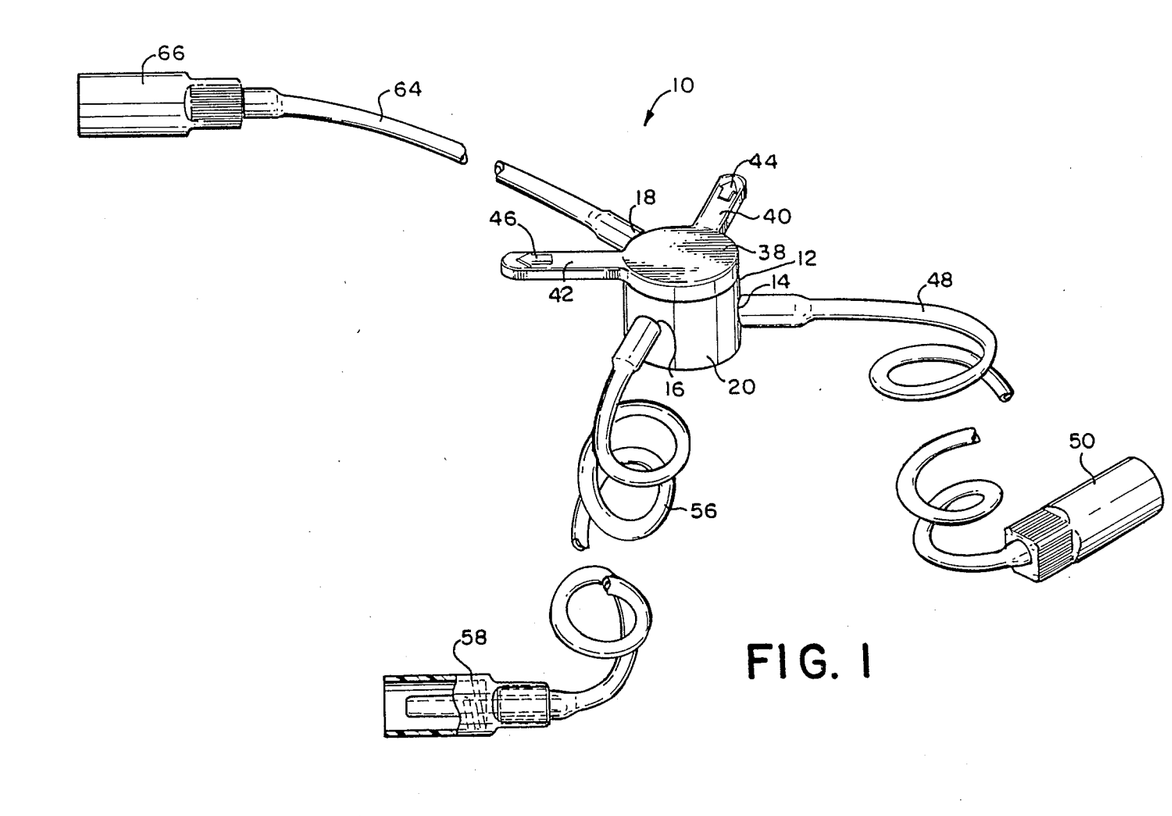
FIG. 1 is a perspective view of a valve and associated tubing and connectors in accordance with the present invention.
Figure 2:
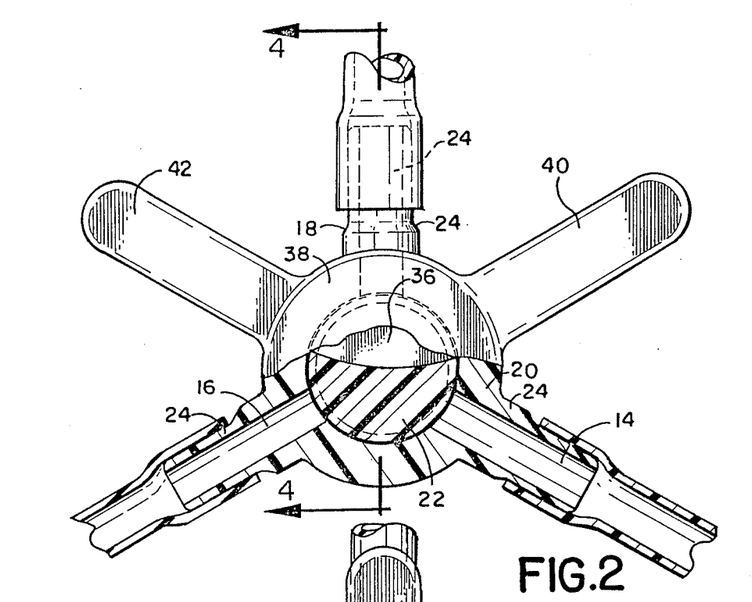
FIG. 2 is an enlarged top plan view, partially in section, of the valve shown in FIG. 1.
Figure 3:
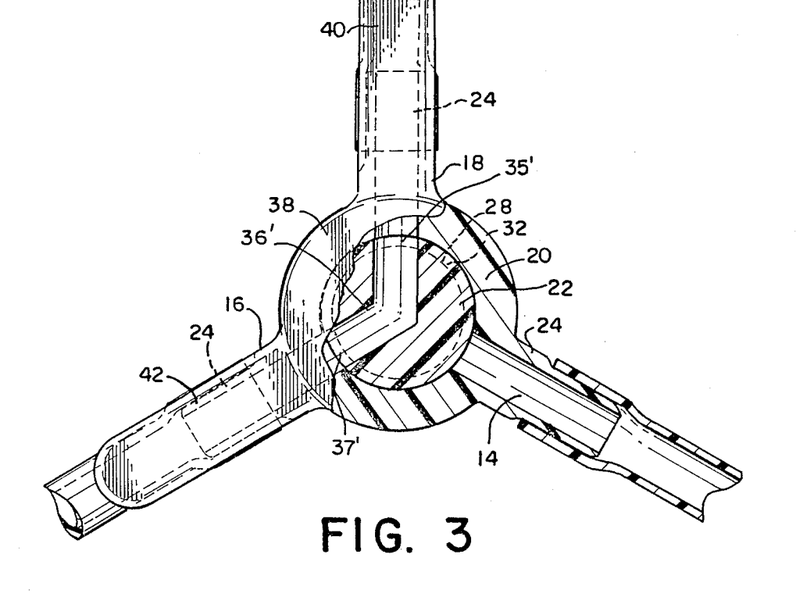
FIG. 3 is an enlarged top plan view, partially in section, of a slight variation of the valve of FIG. 1, with the actuator in a different orientation.
Figure 4:
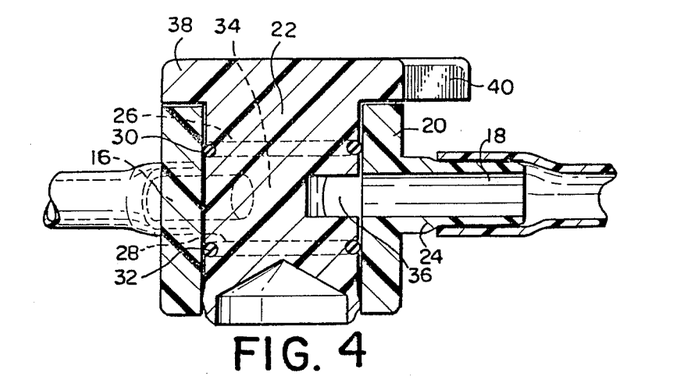
FIG. 4 is a sectional view of the valve taken along lines 4—4 of FIG. 2.

Referring to the drawings, and more particularly to FIG. 1, there is shown an apparatus, generally 10, in accordance with the present invention. The apparatus 10 is comprised of a valve assembly or valve 12 having a first fluid port 14 (hereinafter sometimes referred to as the "A" port), a second fluid port 16 (hereinafter sometimes referred to as the "B" port), and a third fluid port 18 (hereinafter sometimes referred to as the "C" port). In the present embodiment, as best seen in FIGS. 2, 3 and 4, the valve 12 comprises a generally cylindrical or annular housing 20, which generally surrounds a generally cylindrical core member or actuator 22. In the present embodiment, the housing 20 is preferably formed by injection molding of a transparent or translucent plastic material, such as Mobay Merlon M40LRF 1000 Natural, Makrolon 2858 Natural or some other polycarbonate. As best seen in FIGS. 2 and 3, the fluid ports 14, 16 and 18 are positioned at spaced locations around the circumference of the housing 20, generally about 120 degrees apart. Each of the fluid ports 14, 16 and 18 includes a radially outwardly extending generally cylindrical nipple 24 integrally molded with the housing 20. As best seen in FIGS. 2 and 3, the outer end of each of the nipples 24 is slightly tapered to facilitate connection with a length of tubing. Fluid communication is provided between the outer end of each nipple 24 and the interior of the housing 20.

Figure 5:
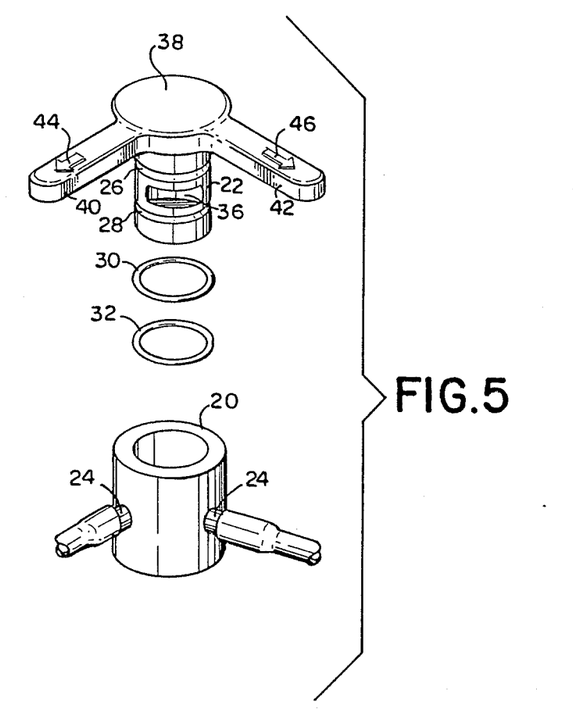
FIG. 5 is a slightly enlarged exploded perspective view of the valve of FIG. 1.

In the present embodiment, the core member or actuator 22 is also injection molded of a plastic material, preferably a polypropylene, such as Vestolen 5202(Huls) or Profax 6523 with 5% Eastman Tenite 1830A by weight. The actuator 22 has an outer diameter which is slightly greater than the inner diameter of the housing 20 to provide a tightly sealed fit when the actuator 22 is installed within the housing 20, as shown in FIG. 4. A lubricant, such as Dow Silicone 360, may be used between the housing 20 and the actuator 22 to facilitate relative movement. The actuator 22 further includes generally annular grooves 26 and 28 extending around the outer circumference, as shown in FIGS. 4 and 5. The grooves 26 and 28 are adapted to receive suitably sized sealing "O" rings 30 and 32, preferably formed of an elastomeric material, such as silicone, for example, Silicone 7621 Natural. As best seen in FIG. 4, when the valve 12 is assembled, the grooves 26 and 28 are located on both axial sides of the fluid ports 14, 16 and 18. In this manner, the grooves 26 and 28 and the "O" rings 30 and 32 cooperate with the interior of the housing 20 to form a fluid-tight seal on both sides of the fluid ports 14, 16 and 18. The combination of the seal formed between the interior of the housing 20 and the exterior of the actuator 22 and the seals formed by the grooves 26 and 28, "O" rings 30 and 32 and the interior of the housing 20 provide a double-sealed barrier to effectively maintain the sterility of the interface area 34 within the housing 20 around the fluid ports 14, 16 and 18, and to prevent the migration of organisms into the interface area 34.

The actuator 22 includes a generally arcuate passageway 36 located axially between the grooves 26 and 28 and extending around a portion of the circumference of the actuator 22. As best shown in FIG. 2, the passageway 36 is adapted to provide fluid communication between any two of the fluid ports 14, 16 and 18, depending upon its position with respect to the housing 20. For purposes which will hereinafter become apparent, the cross-sectional area of the passageway 36 is at least slightly greater than the cross-sectional area of any of the fluid ports 14, 16 and 18.

FIG. 3 shows a slight variation of the valve 12, in which the passageway 36' is comprised of two generally cylindrical bores 35' and 37' which intersect proximate the axial center of the actuator 22. The two bores 35' and 37' extend at an angle of about 120 degrees from each other. The passageway 36' is presently preferred to passageway 36 shown in FIG. 2.

As best shown in FIGS. 1 and 5, the upper end of the actuator 22 includes an enlarged diameter disk-like portion 38. In the present embodiment, the diameter of the disk-like portion 38 generally corresponds to the outer diameter of the housing 20 so that when installing the actuator 22 within the housing 20, the disk-like portion 38 acts as a stop means to indicate that the actuator 22 has been properly installed within the housing 20. The lower portion of the actuator 22 also includes locking means, such as an annular flange (not shown) which engages the lower surface of the housing 20 to retain the actuator 22 in place within the housing 20. The disk-like portion 38 includes a pair of generally radially outwardly extending actuator or arm members 40 and 42. The arm members 40 and 42 are generally spaced about 120 degrees apart and are generally of the same thickness as the remainder of the disk-like portion 38. The arm members 40 and 42 facilitate rotational movement of the actuator 22 with respect to the housing 20. As best shown in FIG. 2, the passageway 36 generally extends between the arm members 40 and 42. Thus, the arm members 40 and 42 may be employed to indicate the location of the passageway 36 to a user. For this purpose, each of the arm members 40 and 42 includes an indicating means, such as arrows 44 and 46, for indicating the fluid flow path through the valve 12 in a manner which will hereinafter become apparent.

As best shown in FIGS. 1 through 4, a first length of tubing or tube 48 has one end which is secured to the first fluid port 14. As best seen in FIGS. 2 and 3, the interior diameter of the first tube 48 is slightly less than the outer diameter of the nipple 24 associated with the first fluid port 14 to provide a tight fit. The first tube 48 is preferably formed of a thermoplastic material such as medical grade polyurethane, for example, extruded Dow 2363 80AE resin. One end of the first tube 48 is bonded to the nipple 24 utilizing a suitable adhesive, such as cyanocrayte or some other thermosetting polyurethane-based adhesive material. As best seen in FIG. 1, the first tube 48 is generally coiled to provide a resilient, self-storing coil which is adapted to preclude tangling or confusion and to prevent possible improper connections which could result from crossing the first tube 48 with other tubes which will hereinafter be described. The coil is formed into the tubing utilizing a thermosetting process.

The other or distal end of the first tube 48 is secured to a first connector member 50, best seen in FIG. 1. The other end of the first tube 48 is secured to the first connector member 50 in substantially the same manner as the one end of the first tube 48 is secured to the nipple 24 of the first fluid port 14.

The first connector member 50 is of a type which is well known in the dialysis art. A detailed description of the structure of the first connector member 50 is not necessary for a complete understanding of the present invention and, therefore, will not be presented herein. Suffice it to say that the first connector member 50 is preferably injection molded of the same material as the valve housing 20 and is adapted to be connected to a complementary mating connector member 52 (shown schematically in FIG. 6a) which is associated with a first fluid container 54 (shown schematically in FIG. 6a). The connection between the first connector member 50 and the mating connector member 52 is generally fluid tight and preferably has at least two seals to maintain sterility and to prevent the migration of organisms into the first tube 48 or into the first fluid container 54. The various components are secured together in this manner to provide direct, unobstructed fluid communication between the first fluid port 14 and the first fluid container 54.

In a similar manner, a second length of tubing or second tube 56 has one end secured to the second fluid port 16 in substantially the same manner that the first tube 48 was secured to the first fluid port 14. The second tube 56 is formed of the same material as the first tube 48. Like the first tube, the second tube 56 is formed into a resilient self-storing coil, and the other or distal end is secured to a second connector member 58. The second connector member 58, which in the present embodiment is structurally the same as the first connector member 50, is adapted to be connected with a fluid tight, sealed connection to a complementary or mating connector member 60 (shown schematically in FIG. 6a) which is associated with a second fluid container 62 (shown schematically in FIG. 6a). The components are connected in this manner to provide direct, unobstructed fluid communication between the second fluid port 16 and the second fluid container 62.

Figure 6A:
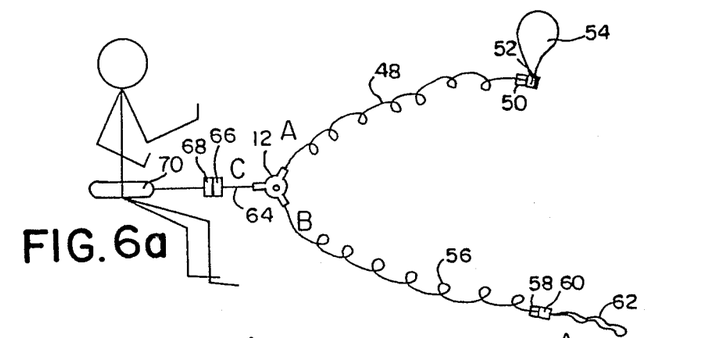
FIGS. 6a through FIG. 6f are schematic representations of the valve of FIG. 1 and associated tubes and connectors for purposes of illustrating the method of the present invention.
Figures 6B, 6C, 6D, 6E, 6F:
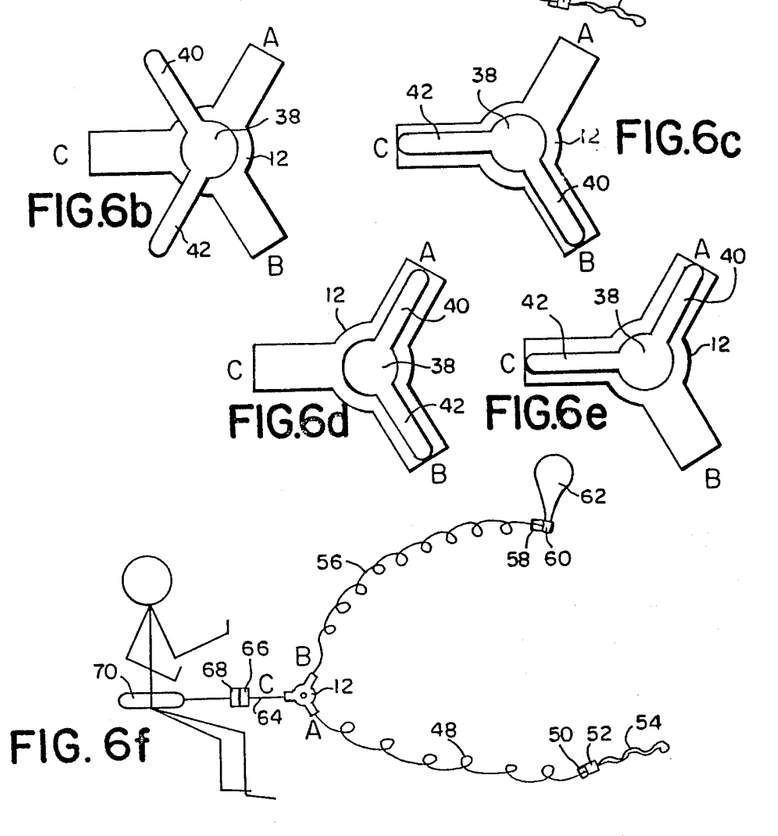

As will hereinafter become apparent, in the present embodiment the first and second fluid containers 54 and 62 are plastic bags, preferably approximately two liters in capacity, of the type well known in the dialysis art. In each cycle of the peritoneal dialysis, one of the fluid containers 54 or 62 contains a quantity of fresh or unused dialysate fluid which is held in an elevated position for infusion into the peritoneal cavity of the user in a manner which will hereinafter be described. Similarly, during the same dialysis cycle, the other fluid container 54 or 62 is initially in an empty condition and serves to collect used or spent dialysate fluid and the toxins contained therein, after an appropriate dwell period within the peritoneal cavity of a user. In some dialysis cycles, such as is illustrated in FIG. 6a, the first fluid container 54 contains the new dialysate fluid and the second fluid container 62 is adapted to receive the used or spent dialysate fluid. In alternate dialysis cycles, such as illustrated in FIG. 6f, the second fluid container 62 contains the fresh dialysate fluid, while the first fluid container 54 is employed to receive the spent dialysate fluid and the toxins. Further details concerning the operation of the apparatus 10 will hereinafter be presented.

Referring again to FIG. 1, it can be seen that a third length of tubing or tube 64 has one end secured to the third fluid port 18 in a manner substantially the same as discussed above with respect to the first tube 48. In the present embodiment, the third tube 64 is formed of the same material as the first and second tubes 48 and 56, but is generally straight, however, it could be coiled, if desired. The other or distal end of the third tube 64 is secured to a third connector member 66 in the same manner in which the first tube 48 is secured to the first connector member 50. The third connector member 66, in the present embodiment, is structurally the same as the first connector member 50. The third connector member 66 is adapted to be connected to a complementary or mating connector member 68 (shown schematically in FIG. 6a) which is associated with a catheter 70 (shown schematically in FIG. 6a) which has previously been surgically implanted in the abdominal wall of the user. As with the previously described connections, the connection between the third connector member 66 and the mating connecting member 68 is of the type well known in the dialysis art, and is designed to provide double sealing to maintain sterility within the catheter 70 and the third tube 64, and to prevent the migration of organisms through the connection. The components are connected together in this manner to provide direct, unobstructed fluid communication between the third fluid port 18 and the peritoneal cavity of the user.

It will be appreciated by those skilled in the art that the particular means of interconnecting the valve 12 with the first and second containers 54 and 62 and with the catheter 70, while shown for the purpose of illustrating the present invention, need not be precisely of the same type shown. In addition, while in the embodiment shown each of the connector members 50, 58 and 66 are indicated as being structurally the same, they could be structurally different. For example, the connector members 50 and 58 adapted for interconnecting with the mating connector members 52 and 60 associated with the first and second fluid containers 54 and 62 could be male connector members as shown, while the third connector member 66 could be of the female type. It should therefore be appreciated that the connector members shown are merely for the purposes of illustration and are not intended to be a limitation on the present invention.

Referring now to FIGS. 2 and 3, it is apparent that the valve actuator 22 is moveable or rotatable with respect to the valve housing 20 to at least four operational positions. In the first position, illustrated in FIG. 2 and FIG. 6b, the passageway 36 within the actuator 22 is in fluid communication only with a single fluid port such as the third fluid port 18. Thus, in the first position of the actuator 22, all of the valve fluid ports 14, 16 and 18 are effectively blocked so that no dialysate fluid may flow through the valve 12 or the apparatus 10. The valve actuator 22 may be moved or rotated to a second position, as illustrated in FIGS. 3 and 6c, in which the passageway 36 (or 36′) provides fluid communication between the second fluid port 16 and the third fluid port 18. In the second position of the actuator 22, dialysate fluid may flow between the second fluid container 62 and the peritoneal cavity of the user. When the valve actuator 22 is moved to a third position, illustrated by FIG. 6d, the passageway 36 provides fluid communication between the first fluid port 14 and the second fluid port 16, thereby permitting fluid to flow between the first and second fluid containers 54 and 62. Finally, when the valve actuator is moved to a fourth position, as illustrated by FIG. 6e, the passageway 36 provides fluid communication between the first fluid port 14 and the third fluid port 18, thereby permitting dialysate fluid to flow between the first fluid container 54 and the peritoneal cavity of the user.

The foregoing description pertains to the structure of the apparatus 10 for bagless CAPD. What follows is a description of a preferred method of operation of the apparatus 10 in performing bagless CAPD. In describing the operation and method of the present invention, two complete CAPD cycles will be discussed.

It will be assumed for purposes of illustrating the present invention that the apparatus is not connected to the user but is positioned in the manner described above and as illustrated in FIG. 6a. In the condition shown in FIG. 6a, the first fluid container 54 contains a fresh supply of dialysate fluid and is suspended by any suitable suspension means, such as a drip stand (not shown) so that the lowest portion of the first fluid container 54 is at a height greater than the catheter 70 or the peritoneal cavity of the user. In addition, the second fluid container 62 is generally empty and is lower than the catheter 70 or the peritoneal cavity of the user. The valve actuator 22 is in the first position, as shown in FIG. 6b, so that no dialysate fluid flows through the apparatus 10. The user has previously undergone dialysate infusion and has just completed the dwell period, so that the user is ready to drain the dialysate from the peritoneal cavity.

The apparatus 10 is connected to the user by conecting the third connector member 66 to its mating connector member 68. The user first turns the valve actuator 22 approximately 60 degrees in the counterclockwise direction to the position shown in FIG. 6c. In doing so, fluid communication is established between the second fluid port 16 and the third fluid port 18 to establish a complete fluid path from the peritoneal cavity to the second fluid container 62. In this manner, the used dialysate fluid within the peritoneal cavity, along with any toxins contained therein, drains from the peritoneal cavity through the valve 12 and into the second fluid container 62.

Once the drainage of the used dialysate fluid has been completed and the second fluid container 62 is filled, the valve actuator 22 is rotated approximately 120 degrees in the counterclockwise direction to the third actuator position shown in FIG. 6d. With the valve actuator 22 in the third position, fluid communication is established between the first fluid port 14 and the second fluid port 16. In this manner, fresh dialysate fluid from the first fluid container 54 flows through the valve 12 to flush from the valve 12, and particularly from the passageway 36, any remaining used dialysate fluid and/or toxins, as well as contaminants which may have been introduced when the fresh bag of dialysate was connected. The flushing action occurs only for a very brief period of time, preferably about ten seconds.

Once the valve 12 has been flushed, the valve actuator 22 is again rotated approximately 120 degrees in the counterclockwise direction to the fourth position, as illustrated in FIG. 6e. In the fourth position, the passageway 36 provides fluid communication between the first fluid port 14 and the third fluid port 18. In this manner, fresh dialysate fluid from the first container 54 flows through the valve 12 and into the peritoneal cavity of the user.

Preferably, while the fresh dialysate fluid is being infused into the peritoneal cavity of the user, the user disconnects the second connector member 58 from the mating connector member 60, thereby removing the second fluid container 62 for disposal. Thereafter, a new second fluid container 62 having a new mating connector member 60 is attached to the second connector member 58 after suitable sterilization in accordance with techniques well known in the dialysate art. The new second fluid container 62 contains a fresh supply of dialysate fluid. When the first fluid container 54 is empty, the valve actuator 22 is rotated approximately 60 degrees in the counterclockwise direction to the first position, as illustrated in FIG. 6b. As previously indicated, in the first valve actuator position, all of the fluid ports 14, 16 and 18 are blocked so that no dialysate fluid flows through the valve 12. The user then disconnects the third connector member 66 from its mating connector member 68 and covers the mating connector member 68 with a suitable cover (not shown) of a type and in a manner well known in the dialysis art. The user is then free to conduct his or her normal activities during the dwell period of the dialysate fluid. The user may raise the second fluid container above the level of the catheter 70 and correspondingly lower the first fluid container 54 to a position lower than the level of the catheter 70, as best seen in FIG. 6f, either before or after the dwell period. Thus, after the dwell period, the second fluid container 62 serves as the source of fresh dialysate fluid and the first fluid container 54 serves to collect the used dialysate fluid.

When the dwell period has expired, the user removes the protective cap from the mating connector member 68 and, after proper cleaning and/or sterilization, reconnects the third connector member 66 with the mating connector member 68 so that the apparatus is again connected substantially as shown in FIG. 6f.

As previously indicated, when the apparatus 10 is reconnected to the user, the fresh dialysate fluid is in the second fluid container 62 and is positioned at a level above that of the catheter 70. The valve actuator 22 is in the first position (FIG. 6b), thereby precluding the flow of dialysate fluid through the apparatus 10. The user then rotates the valve actuator 22 approximately 60 degrees in the clockwise direction to the fourth position as shown in FIG. 6e, thereby permitting fluid from the peritoneal cavity to drain into the first fluid container 54. Once the drainage of the dialysate fluid has been completed, the valve actuator 22 is rotated about 120 degrees in the clockwise direction, to the third position as shown in FIG. 6d, thereby permitting fresh dialysate fluid from the second fluid container 62 to flow through the valve 12 and into the first fluid container 54 to flush the valve and tubing of any remaining used dialysate fluid and/or contaminants. After a short period of time, preferably ten seconds, the valve actuator 22 is rotated 120 degrees in the clockwise direction to the second position (FIG. 6c), thereby permitting fresh dialysate fluid to flow from the second fluid container 62 into the peritoneal cavity. As the dialysate fluid is being infused, the user disconnects the first connector member 50 from the mating connector member 52, thereby removing the first fluid container member 54 for disposal. A new first fluid container 54 with a supply of fresh dialysate fluid and a new mating connector member 52 are attached to the first connector member 50 as described above. Once all of the fresh dialysate fluid has infused into the peritoneal cavity, the valve actuator 22 is rotated approximately 60 degrees in the clockwise direction to the first position as shown in FIG. 6b. The third connector member 66 is again disconnected from the mating connector member 68 and a suitable cover member (not shown) is installed over the mating connector member 68 during the dwell period. Once the dwell period has been completed, the third connector member 66 is reconnected with the mating connector member 68, the positions of the first and second container members 54 and 62 are again reversed and the entire process is repeated.

From the foregoing description of preferred embodiments, it can be seen that the present invention comprises a method and apparatus for bagless continuous ambulatory peritoneal dialysis. The present invention provides the advantage of greater simplicity of operation and improved performance over the prior art CAPD method. It will be recognized by those skilled in the art that changes or modifications could be made to the above-described embodiments without departing from the broad inventive concepts thereof. For example, different types of connectors could be employed and/or larger sized fluid containers could be employed, permitting the valve actuator to go through several complete rotations in a single direction before adding a new dialysate container and interchanging the positions of the first and second fluid containers. It is understood, therefore, that the present invention is not limited to the embodiment specifically disclosed, but is intended to cover everything which is in the scope and spirit of the invention as defined by the appended claims.

What is claimed is:

1. A system for continuous ambulatory peritoneal dialysis apparatus, comprising:
   a valve having first, second and third fluid ports;
   a first tube having one end secured to the first fluid port and the other end secured to a first connector member, the first connector member being connectable to a mating connector member associated with a first fluid container to provide fluid communication between the first fluid port and the first fluid container;
   a second tube having one end secured to the second fluid port and the other end secured to a second connector member, the second connector member being connectable to a mating connector member associated with a second fluid container to provide fluid communication between the second fluid port and the second fluid container; and
   a third tube having one end secured to the third fluid port and the other end secured to a third connector member, the third connector member being connectable to a mating connector member associated with a catheter which has been surgically implanted in the abdominal wall of a user to provide fluid communication between the third fluid port and the peritoneal cavity of the user, the valve including an actuator moveable sequentially in either order between four positions, a first position in which all of the fluid ports are blocked to prevent the flow of fluid through the valve, a second position in which only the second and third fluid ports are interconnected to provide bi-directional fluid communication therebetween, a third position in which only the first and second fluid ports are interconnected to provide bi-directional fluid communication therebetween, and a fourth position in which only the first and third fluid ports are interconnected to provide bi-directional fluid communication therebetween, the location of the fluid ports and the structure of the actuator being established in a manner so that movement of the actuator between the second and third positions, in either direction, does not result in movement of the actuator through the fourth position and movement of the actuator between the third and fourth positions, in either direction, does not result in movement of the actuator through the second position, the system having a first configuration wherein said first connector member is located at a higher elevation than said third connector member, and wherein said second connector member is located at a lower elevation than said third connector member, such that fluid flows through the valve in a first direction only from said third port to said second port, from said first port to said second port and from said first port to said third port, the system having a second configuration wherein said second connector member is located at an elevation higher than said third connector member, and wherein said first connector member is located at a lower elevation than said third connector member, such that fluid flows through the valve in a second direction only from said third port to said first port, from said second port to said first port and from said second port to said third port.

2. The apparatus as recited in claim 1, wherein the actuator is rotatable between said four positions, the actuator being rotated generally 360 degrees in steps in a first direction for completion of a first dialysis cycle and the actuator being rotated generally 360 degrees in steps in the other direction for completion of a second dialysis cycle.

3. The apparatus as recited in claim 1, wherein the valve comprises a generally cylindrical housing, the fluid ports being positioned around the circumference of the housing and being spaced apart approximately 120°.

4. A method for performing continuous ambulatory peritoneal dialysis utilizing a valve having first, second and third ports, the first port being in fluid communication with a first fluid container, the second port being in fluid communication with a second fluid container, and the third port being in fluid communication with the peritoneal cavity of the user, the valve including an actuator moveable between four positions, a first position in which all of the fluid ports are blocked to prevent flow of fluid to the valve, a second position in which the second and third fluid ports are interconnected to provide fluid communication therebetween, a third position in which the first and second fluid ports are interconnected to provide fluid communication therebetween, and a fourth position in which the first and third fluid ports are interconnected to provide fluid communication therebetween, the method comprising the steps of:

(a) supporting the first fluid container at a height above the peritoneal cavity of the user and providing the first fluid container with a supply of dialysate fluid;

(b) supporting the second fluid container at a position below the peritoneal cavity, the second fluid container being generally empty;

(c) connecting the valve with the actuator in the first position to the user after a dialysate dwell period;

(d) moving the valve actuator to the second position to permit used dialysate fluid to drain from the peritoneal cavity into the second fluid container;

(e) moving the valve actuator to the third position to permit dialysate fluid to flow from the first fluid container through the valve to the second fluid container to flush the valve;

(f) moving the valve actuator to the fourth position to permit dialysate fluid to flow from the first container into the peritoneal cavity;

(g) removing and disposing of the second fluid container with the used dialysate fluid and replacing it with a second fluid container having a supply of fresh dialysate fluid;

(h) moving the valve actuator to the first position to prevent fluid flow through the valve;

(i) supporting the second fluid container at a position above the height of the peritoneal cavity, and supporting the first fluid container at a position below the peritoneal cavity;

(j) disconnecting the valve from the user for a dialysate dwell period;

(k) reconnecting the valve to the user when the dialysate dwell period has been completed;

(l) moving the actuator to the fourth position to permit used dialysate fluid from the peritoneal cavity to drain into the first fluid container;

(m) moving the valve actuator to the third position to permit dialysate fluid to flow from the second fluid container through the valve to the first fluid container to flush the valve;

(n) moving the valve actuator to the second position to permit dialysate fluid to flow from the second fluid container into the peritoneal cavity;

(o) removing and disposing of the first fluid container with the used dialysate fluid and replacing it with a new first fluid container having a supply of fresh dialysate fluid;

(p) moving the valve actuator to the first position to prevent fluid flow through the valve; and (q) disconnecting the valve from the user for a dialysate dwell period.

5. The method as recited in claim 4 wherein the valve is connected to the first and second containers utilizing connector assemblies.

6. The method as recited in claim 4 wherein the valve is connected to the peritoneal cavity of the user utilizing a surgically implanted catheter and a connector assembly.

* * * * *